(12) United States Patent
Fang et al.

(10) Patent No.: US 11,977,014 B2
(45) Date of Patent: May 7, 2024

(54) SYSTEMS AND METHODS FOR ANALYZING DIFFUSION TREND OF DIFFUSIBLE SUBSTANCE

(71) Applicant: ZHEJIANG DAHUA TECHNOLOGY CO., LTD., Zhejiang (CN)

(72) Inventors: Yongjun Fang, Hangzhou (CN); Guoquan Zhang, Hangzhou (CN); Zhiji Deng, Hangzhou (CN)

(73) Assignee: ZHEJIANG DAHUA TECHNOLOGY CO., LTD., Hangzhou (CN)

( * ) Notice: Subject to any disclaimer, the term of this patent is extended or adjusted under 35 U.S.C. 154(b) by 283 days.

(21) Appl. No.: 17/655,993

(22) Filed: Mar. 22, 2022

(65) Prior Publication Data

US 2022/0214258 A1 Jul. 7, 2022

Related U.S. Application Data

(63) Continuation of application No. PCT/CN2020/120367, filed on Oct. 12, 2020.

(30) Foreign Application Priority Data

Oct. 14, 2019 (CN) .............................. 201910974798

(51) Int. Cl.
  *G08B 21/00* (2006.01)
  *G01N 13/00* (2006.01)
  *G08B 21/12* (2006.01)
(52) U.S. Cl.
  CPC ............. *G01N 13/00* (2013.01); *G08B 21/12* (2013.01); *G01N 2013/003* (2013.01)

(58) Field of Classification Search
  CPC ............. G01N 13/00; G01N 2013/003; G01N 33/0067; G01N 2015/0046; G01N 15/06; G01N 33/0004; G08B 21/12; G01M 3/04
  See application file for complete search history.

(56) References Cited

U.S. PATENT DOCUMENTS

| 8,614,633 B1 * | 12/2013 | Lear ..................... G08B 29/188 340/984 |
| 10,393,856 B2 * | 8/2019 | Johnson .................. H04W 4/02 |

(Continued)

FOREIGN PATENT DOCUMENTS

| CN | 101888718 A | 11/2010 |
| CN | 202394333 U | 8/2012 |

(Continued)

OTHER PUBLICATIONS

Partial Supplementary European Search Report in European Application No. 20877588.2 dated Dec. 5, 2022, 10 pages.

(Continued)

*Primary Examiner* — Toan N Pham
(74) *Attorney, Agent, or Firm* — METIS IP LLC

(57) ABSTRACT

Systems and methods for analyzing a diffusion trend of a diffusible substance. The systems may obtain a plurality of sets of reference information relating to the diffusible substance from a plurality of devices respectively, each of the plurality of sets of reference information at least including a time point when a corresponding device detects the diffusible substance and a location where the device detects the diffusible substance. The plurality of sets of reference information may correspond to a same or a substantially same time domain. The systems may determine the diffusion trend of the diffusible substance based on the plurality of sets reference information.

20 Claims, 10 Drawing Sheets

(56) References Cited

U.S. PATENT DOCUMENTS

| | | | | |
|---|---|---|---|---|
| 11,710,085 B2* | 7/2023 | Alsahlawi | ............... | G06N 20/00 706/12 |
| 2012/0150755 A1 | 6/2012 | Kumar et al. | | |
| 2014/0349707 A1* | 11/2014 | Bang | ...................... | G08B 21/12 455/556.1 |
| 2017/0193790 A1* | 7/2017 | Cornwall | ............... | G01D 21/00 |
| 2018/0025622 A1 | 1/2018 | Lindoff et al. | | |
| 2018/0299417 A1 | 10/2018 | Cha et al. | | |

FOREIGN PATENT DOCUMENTS

| | | |
|---|---|---|
| CN | 102830400 A | 12/2012 |
| CN | 103512562 A | 1/2014 |
| CN | 105261140 A | 1/2016 |
| CN | 106779185 A | 5/2017 |
| CN | 107144343 A | 9/2017 |
| CN | 207380482 U | 5/2018 |
| CN | 108282756 A | 7/2018 |
| CN | 108961631 A | 12/2018 |
| CN | 108990006 A | 12/2018 |
| CN | 109657310 A | 4/2019 |
| CN | 109903490 A | 6/2019 |
| KR | 101686587 B1 | 12/2016 |
| KR | 20180090933 A | 8/2018 |
| WO | 2021073474 A1 | 4/2021 |

OTHER PUBLICATIONS

The Communication Pursuant to Article 94(3) EPC in European Application No. 20877588.2 dated Oct. 6, 2023, 3 pages.
International Search Report in PCT/CN2020/120367 dated Jan. 12, 2021, 5 pages.
Written Opinion in PCT/CN2020/120367 dated Jan. 12, 2021, 6 pages.
First Office Action in Chinese Application No. 201910974798.2 dated Mar. 3, 2021, 22 pages.
Wang, Yanqiu et al., Study on Diversified System for Fire Automatic Detecting & Alarming, Electronic Measurement Technology, 42(4): 42-46. 2019.

* cited by examiner

600

Obtaining a plurality of sets of reference information relating to a diffusible substance from a plurality of devices respectively — 610

Determining a diffusion trend of the diffusible substance based at least in part on the plurality of sets reference information — 620

FIG. 6

SYSTEMS AND METHODS FOR ANALYZING DIFFUSION TREND OF DIFFUSIBLE SUBSTANCE

CROSS-REFERENCE TO RELATED APPLICATIONS

This application is a Continuation of International Application No. PCT/CN2020/120367, filed on Oct. 12, 2020, which claims priority of Chinese Patent Application No. 201910974798.2, filed on Oct. 14, 2019, the entire content of which is incorporated herein by reference.

TECHNICAL FIELD

The present disclosure generally relates to the field of scene monitoring, and in particular, to systems and methods for analyzing a diffusion trend of a diffusible substance.

BACKGROUND

Leakage of a diffusible substance (e.g., a harmful gas) usually poses potential hazards to life and property safety. Commonly, a monitoring system uses a single device or a set of devices with the same type to detect the diffusible substance, which can only achieve local regional diffusion monitoring and limited-dimensional diffusion monitoring. In addition, although a plurality of devices with different types can be applied in some situations, time synchronization of the plurality of devices can't be achieved, which results in that the diffusion monitoring result is inaccurate. Therefore, it is desirable to provide systems and methods for analyzing a diffusion trend of a diffusible substance accurately and efficiently, thereby determining a response plan for dealing with the diffusible substance to prevent the safety hazard caused by the diffusible substance.

SUMMARY

In another aspect of the present disclosure, a system for analyzing a diffusion trend of a diffusible substance is provided. The system may include at least one storage device including a set of instructions and at least one processor in communication with the at least one storage device. When executing the set of instructions, the at least one processor may be directed to cause the system to perform following operations. The system may obtain a plurality of sets of reference information relating to the diffusible substance from a plurality of devices respectively. Each of the plurality of sets of reference information at least may include a time point when a corresponding device detects the diffusible substance and a location where the device detects the diffusible substance. The plurality of sets of reference information may correspond to a same or a substantially same time domain. The system may determine the diffusion trend of the diffusible substance based on the plurality of sets reference information.

In some embodiments, the obtaining the plurality of sets of reference information relating to the diffusible substance from the plurality of devices respectively may include obtaining, via a network satisfying a predetermined time delay condition, the plurality of sets of reference information relating to the diffusible substance from the plurality of devices respectively.

In some embodiments, a time delay of the network may be less than a predetermined delay threshold.

In some embodiments, the obtaining the plurality of sets of reference information relating to the diffusible substance from the plurality of devices respectively may include obtaining a plurality of sets of preliminary reference information relating to the diffusible substance from a plurality of devices respectively and determining the plurality of sets of reference information relating to the diffusible substance by calibrating the plurality of sets of preliminary reference information to be corresponding to a same or a substantially same time domain.

In some embodiments, each of the plurality of sets of reference information may further include an indicator reflecting an amount of the diffusible substance at the time point when the diffusible substance is detected by the corresponding device and the location where the diffusible substance is detected by the corresponding device.

In some embodiments, the diffusible substance may include a gas or a powder, and the indicator may include a concentration of the gas or the powder. Alternatively, the diffusible substance may include a liquid, and the indicator may include a hydraulic pressure of the liquid.

In some embodiments, each of the plurality of sets of reference information may further include sound information relating to the diffusible substance at the time point when the diffusible substance is detected by the corresponding device and the location where the diffusible substance is detected by the corresponding device.

In some embodiments, each of the plurality of sets of reference information may further include environmental information at the time point when the diffusible substance is detected by the corresponding device and the location where the diffusible substance is detected by the corresponding device.

In some embodiments, the environmental information may include at least one of a temperature, a humidity, a brightness, an air pressure, a wind direction, or a wind speed.

In some embodiments, the diffusion trend may include at least one of a diffusion direction, a diffusion speed, or a diffusion path.

In some embodiments, the determining the diffusion trend of the diffusible substance based on the plurality of sets reference information may include ranking the plurality of sets of reference information based on a plurality of time points corresponding to the plurality of sets of reference information and determining the diffusion trend of the diffusible substance based on a ranking result.

In some embodiments, the operations may further include determining, based on the diffusion trend of the diffusible substance, a response plan for dealing with the diffusible substance.

In some embodiments, the operations may further include transmitting the response plan to a target terminal.

In another aspect of the present disclosure, a method for analyzing a diffusion trend of a diffusible substance is provided. The method may be implemented on a computing device including at least one processor and at least one storage device. The method may include obtaining a plurality of sets of reference information relating to the diffusible substance from a plurality of devices respectively. Each of the plurality of sets of reference information may at least include a time point when a corresponding device detects the diffusible substance and a location where the device detects the diffusible substance. The plurality of sets of reference information may correspond to a same or a substantially same time domain. The method may also include determining the diffusion trend of the diffusible substance based on the plurality of sets reference information.

In some embodiments, the obtaining the plurality of sets of reference information relating to the diffusible substance from the plurality of devices respectively may include obtaining, via a network satisfying a predetermined time delay condition, the plurality of sets of reference information relating to the diffusible substance from the plurality of devices respectively.

In some embodiments, a time delay of the network may be less than a predetermined delay threshold.

In some embodiments, the obtaining the plurality of sets of reference information relating to the diffusible substance from the plurality of devices respectively may include obtaining a plurality of sets of preliminary reference information relating to the diffusible substance from a plurality of devices respectively and determining the plurality of sets of reference information relating to the diffusible substance by calibrating the plurality of sets of preliminary reference information to be corresponding to a same or a substantially same time domain.

In some embodiments, each of the plurality of sets of reference information may further include an indicator reflecting an amount of the diffusible substance at the time point when the diffusible substance is detected by the corresponding device and the location where the diffusible substance is detected by the corresponding device.

In some embodiments, the diffusible substance may include a gas or a powder, and the indicator may include a concentration of the gas or the powder. Alternatively, the diffusible substance may include a liquid, and the indicator may include a hydraulic pressure of the liquid.

In some embodiments, each of the plurality of sets of reference information may further include sound information relating to the diffusible substance at the time point when the diffusible substance is detected by the corresponding device and the location where the diffusible substance is detected by the corresponding device.

In some embodiments, each of the plurality of sets of reference information may further include environmental information at the time point when the diffusible substance is detected by the corresponding device and the location where the diffusible substance is detected by the corresponding device.

In some embodiments, the environmental information may include at least one of a temperature, a humidity, a brightness, an air pressure, a wind direction, or a wind speed.

In some embodiments, the diffusion trend may include at least one of a diffusion direction, a diffusion speed, or a diffusion path.

In some embodiments, the determining the diffusion trend of the diffusible substance based on the plurality of sets reference information may include ranking the plurality of sets of reference information based on a plurality of time points corresponding to the plurality of sets of reference information and determining the diffusion trend of the diffusible substance based on a ranking result.

In some embodiments, the method may further include determining, based on the diffusion trend of the diffusible substance, a response plan for dealing with the diffusible substance.

In some embodiments, the method may further include transmitting the response plan to a target terminal.

In another aspect of the present disclosure, a system for analyzing a diffusion trend of a diffusible substance is provided. The system may include an obtaining module configured to obtain a plurality of sets of reference information relating to the diffusible substance from a plurality of devices respectively. Each of the plurality of sets of reference information may at least include a time point when a corresponding device detects the diffusible substance and a location where the device detects the diffusible substance. The plurality of sets of reference information may correspond to a same or a substantially same time domain. The system may also include a diffusion trend determination module configured to determine the diffusion trend of the diffusible substance based on the plurality of sets reference information.

In another aspect of the present disclosure, a non-transitory computer readable medium including executable instructions for analyzing a diffusion trend of a diffusible substance is provided. When executed by at least one processor, the executable instructions may direct the at least one processor to perform a method. The method may include obtaining a plurality of sets of reference information relating to the diffusible substance from a plurality of devices respectively. Each of the plurality of sets of reference information may at least include a time point when a corresponding device detects the diffusible substance and a location where the device detects the diffusible substance. The plurality of sets of reference information may correspond to a same or a substantially same time domain. The method may also include determining the diffusion trend of the diffusible substance based on the plurality of sets reference information.

In another aspect of the present disclosure, a system for analyzing a diffusion trend of a diffusible substance is provided. The system may include a plurality of devices each of which is configured to detect a set of reference information relating to the diffusible substance. The set of reference information may at least include a time point when a corresponding device detects the diffusible substance and a location where the device detects the diffusible substance. The plurality of devices may correspond to a same or a substantially same time domain. The system may also include at least one processor configured to obtain, via a network, the plurality of sets of reference information from the plurality of devices respectively and determine the diffusion trend of the diffusible substance based on the plurality of sets of reference information.

In some embodiments, at least one of the plurality of devices may include a fixedly mounted device or a movable device.

In some embodiments, a time delay of the network may be less than a predetermined delay threshold.

In some embodiments, each of the plurality of devices may include a positioning sensor configured to detect the location where the corresponding device detects the diffusible substance and a substance sensor configured to detect whether the diffusible substance exists.

In some embodiments, each of the plurality of devices may include an amount sensor configured to determine an indicator indicating an amount of the diffusible substance at the time point when the diffusible substance is detected by the corresponding device and the location where the diffusible substance is detected by the corresponding device.

In some embodiments, each of the plurality of devices may include a sound sensor configured to determine sound information relating to the diffusible substance at the time point when the diffusible substance is detected by the corresponding device and the location where the diffusible substance is detected by the corresponding device.

In some embodiments, each of the plurality of devices may include at least one of a temperature sensor, a humidity sensor, a brightness sensor, an air pressure sensor, or a wind sensor, which is configured to determine environmental information relating to the diffusible substance at the time point when the diffusible substance is detected by the corresponding device and the location where the diffusible substance is detected by the corresponding device.

In some embodiments, the environmental information may include at least one of a temperature, a humidity, a brightness, an air pressure, a wind direction, or a wind speed.

In some embodiments, to determine the diffusion trend of the diffusible substance based on the plurality of sets of reference information, the at least one processor may be configured to rank the plurality of sets of reference information based on a plurality of time points corresponding to the plurality of sets of reference information and determine the diffusion trend of the diffusible substance based a ranking result.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 6 is a flowchart illustrating an exemplary process for determining a diffusion trend of a diffusible substance according to some embodiments of the present disclosure;

DETAILED DESCRIPTION

Figure 1A:
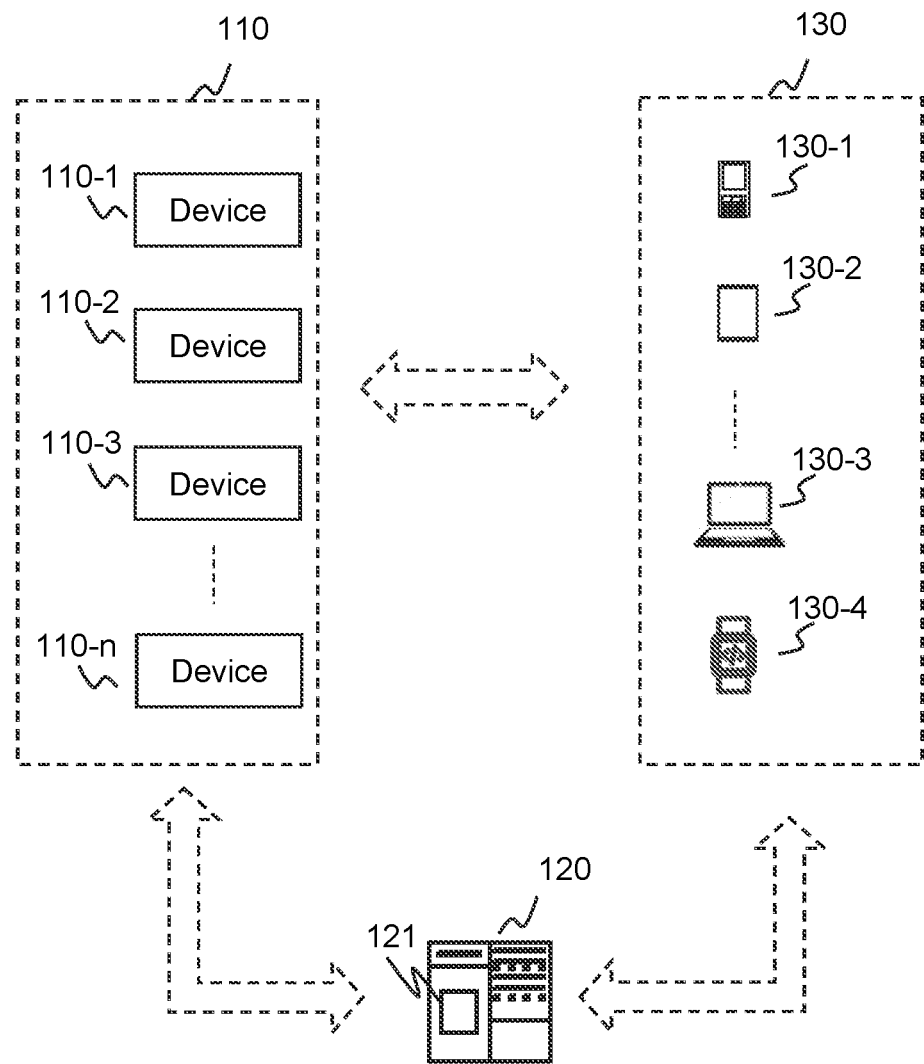
FIGS. 1A-1D are schematic diagrams illustrating an exemplary monitoring system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression(s) if they may achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device(s). In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules (or units or blocks) may be included in connected logic components, such as gates and flip-flops, and/or can be included in programmable units, such as programmable gate arrays or processors. The modules (or units or blocks) or computing device functionality described herein may be implemented as software modules (or units or blocks), but may be represented in hardware or firmware. In general, the modules (or units or blocks) described herein refer to logical modules (or units or blocks) that may be combined with other modules (or units or blocks) or divided into sub-modules (or sub-units or sub-blocks) despite their physical organization or storage.

It will be understood that when a unit, engine, module, or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

An aspect of the present disclosure relates to a system and method for determining a diffusion trend of a diffusible substance. The system may obtain a plurality of sets of reference information relating to the diffusible substance from a plurality of devices respectively. Each of the plurality of sets of reference information at least may include a time point when a corresponding device detects the diffusible substance and a location where the device detects the diffusible substance. The plurality of sets of reference information may correspond to a same or a substantially same time domain. The system may determine the diffusion trend of the diffusible substance based on the plurality of sets reference information.

According to some embodiments of the present disclosure, the reference information relating to the diffusible substance corresponds to a same or a substantially same time domain, such that the diffusion trend determined based on the reference information can reflect a real situation of the diffusible substance accurately. Besides, each of the plurality of devices can acquire a set of reference information which can reflect parameters of the diffusible substance comprehensively and multi-dimensionally. Accordingly, the diffusion trend determined based on the plurality of sets of reference information can reflect the real situation of the diffusible substance comprehensively and multi-dimensionally. Further, the system may determine a response plan for dealing with the diffusible substance based on the diffusion trend of the diffusible substance. According to the response plan, relevant personnel such as a fireman can efficiently deal with the diffusible substance in time, thereby preventing a further diffusion of the diffusible substance and/or reducing the loss or hazard caused by the diffusible substance.

FIG. 1A is a schematic diagram illustrating an exemplary monitoring system according to some embodiments of the present disclosure. The monitoring system 100 may be applied in various scenarios, for example, fire-fighting monitoring, chemical production monitoring, etc. As shown in FIG. 1, the monitoring system 100 may include a plurality of devices 110, a server 120, and one or more terminal devices 130.

The plurality of devices 110 may include a device 110-1, a device 110-2, a device 110-3, . . . , and a device 110-n. As used herein, "a device" is used for brevity, it should be noted that "a device" also can be considered as "a set of devices" with the same type or different types. In some embodiments, each of the plurality of devices 110 may include any monitoring device such as a movable device can enter a monitoring scenario individually or with a user (e.g., a fireman) or a fixedly mounted device in the monitoring scenario. Exemplary movable devices may include a portable device (PD) (e.g., a helmet, a mobile terminal), an unmanned aerial vehicle (UAV), a robot, etc. Exemplary fixedly mounted devices may include an acquisition device (e.g., an image acquisition device, a sound acquisition device, a temperature monitoring device), an alarm device (e.g., a smoke alarm device, a fire alarm device, a gas alarm device), etc.

Figure 1B:
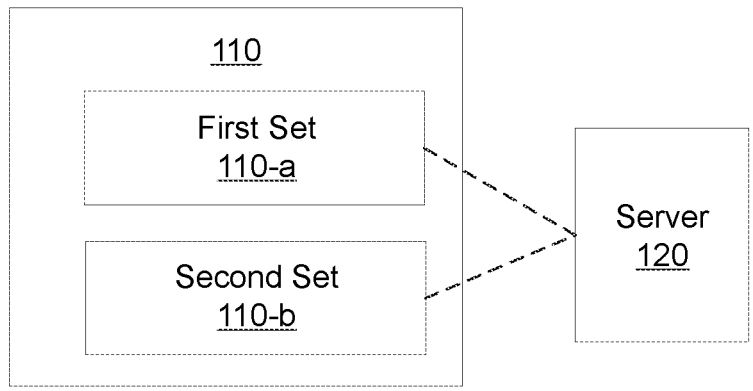
Figure 1C:
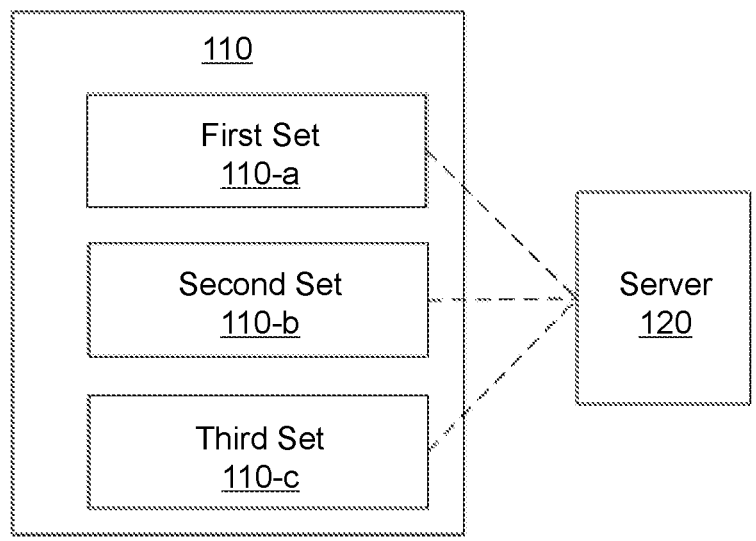
Figure 1D:
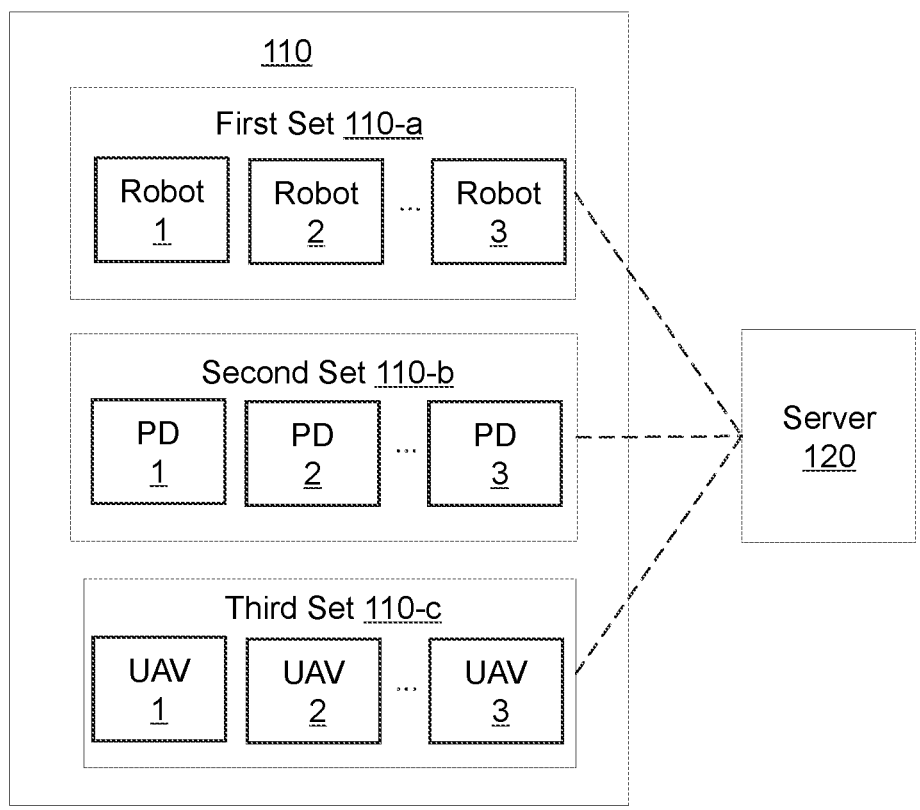

In some embodiments, types of the plurality of devices 110 may be the same or different. For example, as shown in FIG. 1B, the plurality of devices 110 may include a first set of devices 110 (also referred to as "first set 110-$a$" for brevity) with a first type and a second set of devices 110 (also referred to as "second set 110-$b$" for brevity) with a second type. As another example, as shown in FIG. 1C, the plurality of devices 110 may include the first set 110-$a$, the second set 110-$b$, and a third set of devices 110 (also referred to as "third set 110-$c$" for brevity) with a third type. In some embodiments, types of a set of devices (e.g., the first set 110-$a$, the second set 110-$b$, or the third set 110-$c$) may be the same or different. For example, as shown in FIG. 1D, the first set 110-$a$ may include a set of robots (e.g., robot 1, robot 2, . . . , and robot n), the second set 110-$b$ may include a set of PDs (e.g., PD 1, PD 2, . . . , and PD n), and the third set 110-$c$ may include a set of UAVs (e.g., UAV 1, UAV 2, . . . , UAV n).

In some embodiments, the plurality of devices 110 may be connected to the server 120 via a network satisfying a predetermined time delay condition. In some embodiments, the predetermined time delay condition may be a default setting of the monitoring system 100 or may be adjustable under different situations. For example, the plurality of devices 110 may be connected to the server 120 via a network with a time delay less than a predetermined delay threshold (e.g., 1 millisecond, 0.5 milliseconds, 0.2 milliseconds, 0.1 milliseconds). In this situation, the plurality of devices 110 may correspond to a same or a substantially same time domain. Merely by way of example, the plurality of devices 110 may be connected to the server 120 via a 5G network.

In some embodiments, a portion of the plurality of devices 110 may be connected to the server 120 via a network (e.g., a network with a time delay larger than the predetermined delay threshold) that does not satisfy the predetermined time delay condition. In this situation, the portion of the plurality of devices 110 may correspond to different time domains. Accordingly, a calibration may be need to be performed on information acquired by the plurality of devices 110 to make that calibrated information corresponds to a same or a substantially same domain; or a calibration may be need to be performed on the plurality of devices 110 to make that the plurality of devices 110 correspond to a same or a substantially same domain. In some embodiments, the network may include a wired or wireless network such as a cable network, a wireline network, an optical fiber network, a tele communications network, an intranet, an Internet, a local area network (LAN), a wide area network (WAN), a wireless local area network (WLAN), a metropolitan area network (MAN), a public telephone switched network (PSTN), a Bluetooth network, a Zig Bee network, a near field communication (NFC) network, etc. More descriptions regarding the time domain calibration may be found elsewhere in the present disclosure (e.g., FIG. 6 and the descriptions thereof).

In some embodiments, each of the plurality of devices 110 may include one or more sensors configured to detect a set of reference information relating to a diffusible substance. In some embodiments, each of the plurality of devices 110 may upload the set of reference information to other components (e.g., the server 120) of the monitoring system 100 according to a preset time interval (e.g., 0.5 s, 1 s, 2 s, 5 s). In some embodiments, each of the plurality of devices 110 may upload the set of reference information to other components (e.g., the server 120) of the monitoring system 100 in real-time or substantially real-time. In some embodiments, as described above, the plurality of devices 110 may correspond to a same or a substantially same time domain, accordingly, a plurality of sets of reference information corresponding to the plurality of devices 110 may correspond to a same or a substantially same time domain. In some alternative embodiments, as described above, a portion of the plurality of devices 110 may correspond to different time domains, accordingly, the plurality of sets of reference information corresponding to the plurality of devices 110 may correspond to different time domains. In this situation, a calibration may be need to be performed on the plurality of sets of reference information. More descriptions may be found elsewhere in the present disclosure (e.g., FIG. 6 and the description thereof).

In some embodiments, the plurality of devices 110 may include sensors with the same type or different types. In some embodiments, exemplary sensors of the plurality of devices 110 may include a substance sensor (e.g., a gas sensor, a powder sensor, a liquid sensor, an infrared sensor), a timer (e.g., a clock), a positioning sensor (e.g., a global positioning system (GPS) receiver), an amount sensor, a sound sensor, a temperature sensor, a humidity sensor, a brightness sensor, an air pressure sensor, a wind sensor, or the like, or any combination thereof. The substance sensor may be configured to detect whether a diffusible substance exists. The timer may be configured to record a time point when the diffusible substance is detected. The positioning sensor may be configured to detect a location where the diffusible substance is detected. The timer also may be integrated into the positioning sensor. The amount sensor may be configured to determine an indicator indicating an amount of the diffusible substance at a time point when the diffusible substance is detected and a location where the diffusible substance is detected. The sound sensor may be configured to determine sound information relating to the diffusible substance at the time point when the diffusible substance is detected and the location where the diffusible substance is detected. The temperature sensor may be configured to detect a temperature at the time point when the diffusible substance is detected and the location where the diffusible substance is detected. The humidity sensor may be configured to detect a humidity at the time point when the diffusible substance is detected and the location where the diffusible substance is detected. The brightness sensor may be configured to detect a brightness at the time point when the diffusible substance is detected and the location where the diffusible substance is detected. The air pressure sensor may be configured to detect an air pressure at the time point when the diffusible substance is detected and the location where the diffusible substance is detected. The wind sensor may be configured to detect wind information (e.g., a wind direction, a wind speed) at the time point when the diffusible substance is detected and the location where the diffusible substance is detected.

The server 120 may be a single server or a server group. The server group may be centralized or distributed (e.g., the server 120 may be a distributed system). In some embodiments, the server 120 may be local or remote. For example, the server 120 may access information and/or data stored in the plurality of devices 110 and/or the terminal device(s) 130 via a network. As another example, the server 120 may be directly connected to the plurality of devices 110 and/or the terminal device(s) 130 to access stored information and/or data. In some embodiments, the server 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the server 120 may be implemented on a computing device 200 including one or more components illustrated in FIG. 2 of the present disclosure.

In some embodiments, the server 120 may include a processing device 121. The processing device 121 may process information and/or data relating to the diffusible substance to perform one or more functions described in the present disclosure. For example, the processing device 121 may obtain a plurality of sets of reference information relating to a diffusible substance from the plurality of devices 110 respectively. Then the processing device 121 may rank the plurality of sets of reference information based on a plurality of time points corresponding to the plurality of sets of reference information and determine a diffusion trend of the diffusible substance based on a ranking result. As another example, the processing device 121 may determine a response plan for dealing with the diffusible substance based on the diffusion trend. Further, the processing device 121 may transmit the response plan to the terminal device(s) 130 for display and/or further processing. In some embodiments, the processing device 121 may include one or more processing devices (e.g., single-core processing device(s) or multi-core processor(s)). Merely by way of example, the processing device 121 may include a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a controller, a microcontroller unit, a reduced instruction-set computer (RISC), a microprocessor, or the like, or any combination thereof. In some embodiment, the server 120 may be unnecessary and all or part of the functions of the server 120 may be implemented by other components of the monitoring system 100. For example, the processing device 121 may be integrated into a terminal device 130 and the functions (e.g., analyzing the diffusion trend and/or determining the response plan) of the processing device 121 may be implemented by the terminal device 130.

The terminal device(s) 130 may include a mobile device 130-1, a tablet computer 130-2, a laptop computer 130-3, a wearable device 130-4, or the like, or any combination thereof. In some embodiments, the mobile device 130-1 may include a smart home device, a smart mobile device, a virtual reality device, an augmented reality device, or the like, or any combination thereof. The smart home device may include a smart lighting device, a control device of an intelligent electrical apparatus, a smart monitoring device, a smart television, a smart video camera, an interphone, or the like, or any combination thereof. The smart mobile device may include a smartphone, a personal digital assistance (PDA), a gaming device, a navigation device, a point of sale (POS) device, or the like, or any combination thereof. The virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include Google™ Glasses, an Oculus Rift™, a HoloLens™, a Gear VR™, etc. In some embodiments, the wearable device 130-4 may include a smart bracelet, a smart footgear, smart glasses, a smart helmet, a smart watch, smart clothing, a smart backpack, a smart accessory, or the like, or any combination thereof. In some embodiments, the terminal device(s) 130 may be implemented on a computing device 200 including one or more components illustrated in FIG. 2 or a mobile device 300 including one or more components illustrated in FIG. 3 in the present disclosure.

In some embodiments, the terminal device(s) 130 may be configured to facilitate communications between a user (e.g., a fireman) and the monitoring system 100. For example, the user may control a movement of the plurality of devices 110 (e.g., an UAV, a robot) through the terminal device(s) 130. As another example, the user may receive the response plan through the terminal device(s) 130 such that the user can deal with the diffusible substance efficiently and accurately. In some embodiments, a terminal device 130 may be integrated with a device 110 (e.g., a portable device) and functions of the terminal device 130 may be executed by the device 110.

In some embodiments, the monitoring system 100 may also include a storage device (not shown) for storing data and/or instructions that the processing device 121 may execute or use to perform exemplary methods described in the present disclosure. In some embodiments, the storage device may be a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage component 113 may be implemented on a cloud platform. Merely by way of example, the cloud platform may be a private cloud, a public cloud, a hybrid cloud, a community cloud, a distributed cloud, an inter-cloud, a multi-cloud, or the like, or any combination thereof.

It should be noted that the above description regarding the monitoring system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 2:
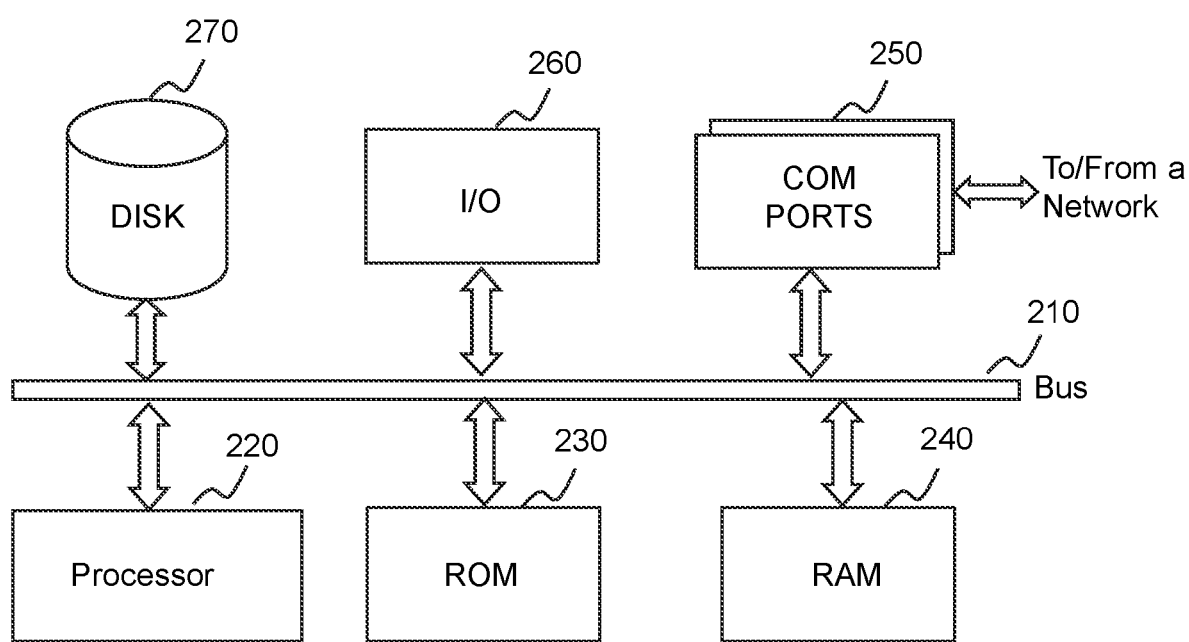
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. The computing device 200 may be used to implement any component of the monitoring system 100 as described herein. For example, the processing device 121 may be implemented on the computing device 200 via its hardware, software program, firmware, or a combination thereof. Although only one such computing device is shown, for convenience, the computer functions relating to the processing device 121 of the monitoring system 100 as described herein may be implemented in a distributed fashion on a number of similar platforms, to distribute the processing load.

The computing device 200, for example, may include COM ports 250 connected to and from a network connected thereto to facilitate data communications. The COM port 250 may be any network port or data exchange port to facilitate data communications. The computing device 200 may also include a processor (e.g., the processor 220), in the form of one or more processors (e.g., logic circuits), for executing program instructions. For example, the processor may include interface circuits and processing circuits therein. The interface circuits may be configured to receive electronic signals from a bus 210, wherein the electronic signals encode structured data and/or instructions for the processing circuits to process. The processing circuits may conduct logic calculations, and then determine a conclusion, a result, and/or an instruction encoded as electronic signals. The processing circuits may also generate electronic signals including the conclusion or the result and a triggering code. In some embodiments, the trigger code may be in a format recognizable by an operation system (or an application installed therein) of an electronic device (e.g., the terminal device(s) 130) in the monitoring system 100. For example, the trigger code may be an instruction, a code, a mark, a symbol, or the like, or any combination thereof, that can activate certain functions and/or operations of a mobile phone or let the mobile phone execute a predetermined program(s). In some embodiments, the trigger code may be configured to rend the operation system (or the application) of the electronic device to generate a presentation of the conclusion or the result (e.g., a prediction result) on an interface of the electronic device. Then the interface circuits may send out the electronic signals from the processing circuits via the bus 210.

The computing device 200 may also include program storage and data storage of different forms including, for example, a disk 270, a read-only memory (ROM) 230, or a random access memory (RAM) 240, for storing various data files to be processed and/or transmitted by the computing device 200. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. Exemplary RAM may include a dynamic RAM (DRAM), a synchronous dynamic RAN (SDRAN), an enhanced synchronous dynamic RAM (ESDRAM), a synchlink dynamic RAM (SLDRAM), a Rambus dynamic RAM (RDRAM), a Rambus direct RAM (RDRAM'), a direct Rambus dynamic RAM (DRDRAM), a double date rate synchronous dynamic RAM (DDR SDRAM), a static RAM (SRAM), a thyristor RAM (T-RAM), and a zero-capacitor RAM (Z-RAM), etc.

The computing device 200 may also include program instructions stored in the ROM 230, RAM 240, and/or other type of non-transitory storage medium to be executed by the processor 220. The methods and/or processes of the present disclosure may be implemented as the program instructions. The computing device 200 may also include operation systems stored in the ROM 230, RAM 240, and/or other type of non-transitory storage medium to be executed by the processor 220. The program instructions may be compatible with the operation systems for executing the methods and/or processer. The computing device 200 also includes an I/O component 260, supporting input/output between the computing device 200 and other components. The computing device 200 may also receive programming and/or data via network communications.

Merely for illustration, only one processor is illustrated in FIG. 2. Multiple processors are also contemplated; thus, operations and/or method steps performed by one processor as described in the present disclosure may also be jointly or separately performed by the multiple processors. For example, if in the present disclosure the processor of the computing device 200 executes both step A and step B, it should be understood that step A and step B may also be performed by two different processors jointly or separately in the computing device 200 (e.g., the first processor executes step A and the second processor executes step B, or the first and second processors jointly execute steps A and B).

Figure 3:
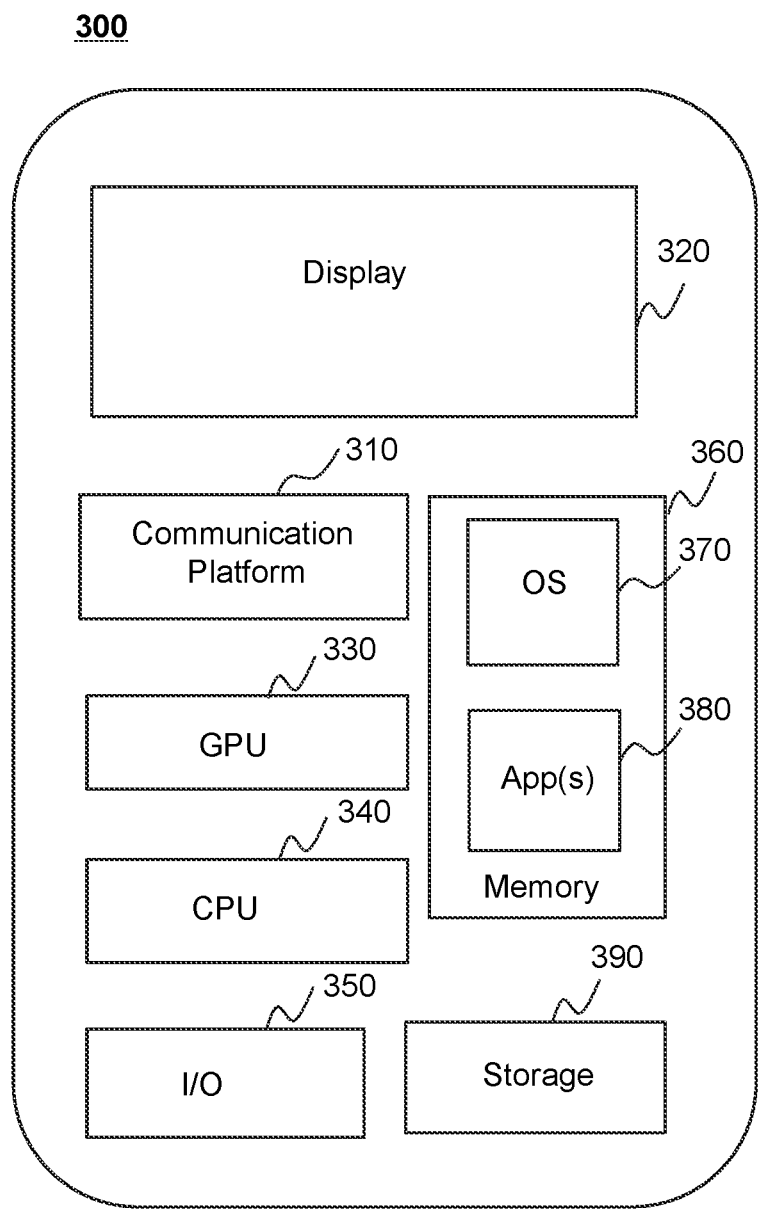
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, one or more components (e.g., the processing device 121, the terminal device 130) of the monitoring system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone) and one or more applications 380 may be loaded into the memory 360 from the storage 390 in order to be executed by the CPU 340. The applications 380 may include a browser or any other suitable mobile apps for receiving and rendering information relating to monitoring or other information from the processing device 121. User interactions with the information stream may be achieved via the I/O 350 and provided to the processing device 121 and/or other components of the monitoring system 100 via a network (e.g., a network as aforementioned elsewhere in the present disclosure).

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
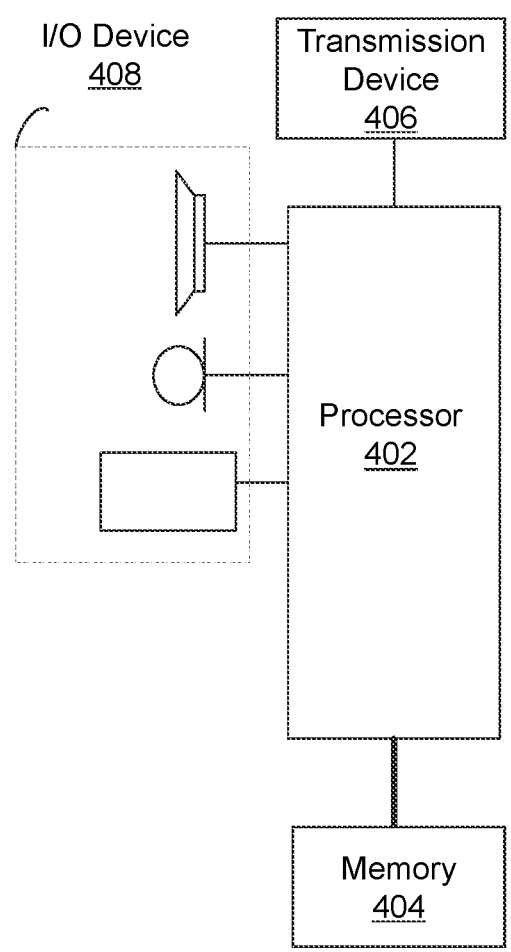
FIG. 4 is a schematic diagram illustrating exemplary components of an exemplary mobile device according to some embodiments of the present disclosure.

FIG. 4 is a schematic diagram illustrating exemplary components of an exemplary mobile device according to some embodiments of the present disclosure. In some embodiments, one or more components (e.g., the processing device 121, the terminal device 130) of the monitoring system 100 may be implemented on the mobile device 400. As shown in FIG. 4, the mobile device 400 may include a processor 402, a memory 404, a transmission device 406, and an I/O device 408.

The processor 402 may include a microprocessor (e.g., a micro control unit, MCU), a programmable logic device (e.g., a FPGA), etc. In some embodiments, the mobile device 400 may include more than one processors to execute functions of the processor 402 jointly or separately. Details regarding the processor(s) 402 may be the same as or similar to that of the processor 220 and/or the CPU 340 as described elsewhere in the present disclosure.

The memory 404 may be configured to store computer programs, for example, software programs and/or modules of applications. For example, the memory 404 may store computer programs corresponding to the methods disclosed elsewhere in the present disclosure. The processor 402 may execute the stored computer programs to perform various functions and/or data processing, thereby achieving the methods. The memory 404 may include high-speed random access memory, a non-volatile memory (e.g., one or more magnetic storage devices, a flash memory, or other non-volatile solid-state memory). In some embodiments, the memory 404 may further include a memory that is set remotely relative to processor 402. The remote memory may be connected to the mobile device 400 via a network. Exemplary network may include an Internet, an intranet, a local area network, a mobile communication network, or the like, or any combination thereof. Details regarding the memory 404 may be the same as or similar to that of the ROM 230, the RAM 240, and/or the memory 360 disclosed elsewhere in the present disclosure.

The transmission device 406 may be configured to achieve communication functions such as receiving or sending data over a network. In some embodiments, the transmission device 406 may include a network interface controller (NIC), which can communicate with the Internet by being connected to other network devices via a base station. In some embodiments, the transmission device 406 may include a radio frequency (RF) module which can be used to communicate wirelessly with the Internet. Details regarding the transmission device 406 may be the same as or similar to that of the communication ports 250 and/or the communication platform 310 disclosed elsewhere in the present disclosure.

Figure 5:
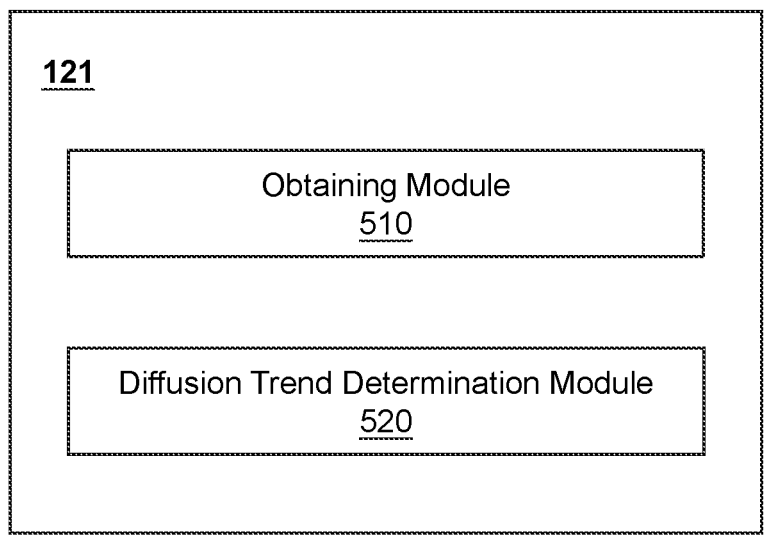
FIG. 5 is a block diagram illustrating an exemplary processing device according to some embodiments of the present disclosure.

FIG. 5 is a block diagram illustrating an exemplary processing device according to some embodiments of the present disclosure. As shown in FIG. 5, the processing device 121 may include an obtaining module 510 and a diffusion trend determination module 520.

The obtaining module 510 may be configured to obtain data/information from one or more components of the firefighting system 100. For example, the obtaining module 510 may obtain a plurality of sets of reference information relating to a diffusible substance from a plurality of devices 110 respectively. The plurality of sets of reference information may correspond to a same or substantially same time domain. The diffusible substance may include a gas, a liquid, a powder, or the like, or any combination thereof. Each of the plurality of sets of reference information may include a time point when a corresponding device 110 detects the diffusible substance, a location where the corresponding device 110 detects the diffusible substance. In some embodiments, each of a portion of the plurality of sets of reference information may include an indicator reflecting an amount of the diffusible substance at the time point and the location. In some embodiments, each of a portion of the plurality of sets of reference information may include sound information relating to the diffusible substance at the time point and the location. In some embodiments, each of a portion of the plurality of sets of reference information may include environmental information at the time point and the location. More descriptions regarding the plurality of set of reference information may be found elsewhere in the present disclosure (e.g., operation 610 and the description thereof).

The diffusion trend determination module 520 may be configured to determine a diffusion trend of the diffusible substance. The diffusion trend may include a diffusion direction, a diffusion path, a diffusion speed, or the like, or any combination thereof. In some embodiments, the diffusion trend may include an amount changing trend. In some embodiments, the diffusion trend determination module 520 may rank the plurality of sets of reference information based on a plurality of sets of time points corresponding to the plurality of sets of reference information and determine the diffusion trend based on a ranking result. More descriptions regarding the determination of the diffusion trend may be found elsewhere in the present disclosure (e.g., operation 620, FIGS. 7 and 8, and the descriptions thereof).

In some embodiments, the processing device 121 may also include a response plan determination module (not shown) configured to determine a response plan for dealing with the diffusible substance. The response plan may relate to a personnel evacuation, a prediction of potential danger, a dealing priority for different locations where the diffusible substance is detected, or the like, or any combination thereof. In some embodiments, the response plan may include a visualization of the diffusion trend. For example, the response plan may include information relating to the diffusion trend mapped on an electronic map and/or presented in a written form. More descriptions regarding the determination of the response plan may be found elsewhere in the present disclosure (e.g., operation 630 and the description thereof).

It should be noted that the above descriptions of the processing device 121 are merely provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure. In some embodiments, two or more of the modules may be combined into a single module, and any one of the modules may be divided into two or more units. For example, the diffusion trend determination module 520 and the response plan determination module may be integrated into a single module. In some embodiments, one or more of the modules mentioned above may be omitted and/or one or more additional modules may be added in the processing device 121. For example, the processing device 121 may further include a storage module. As another example, the processing device 121 may further include a transmission module configured to transmit the response plan to one or more target terminals (e.g., the terminal device(s) 130).

FIG. 6 is a flowchart illustrating an exemplary process for determining a diffusible trend of a diffusible substance according to some embodiments of the present disclosure. In some embodiments, one or more operations in the process 600 may be implemented in the monitoring system 100 illustrated in FIGS. 1A-1D. For example, one or more operations in the process 600 may be stored in a storage device (e.g., the ROM 230, the RAM 240, the storage 390, and/or the memory 404) as a form of instructions, and invoked and/or executed by the processing device 121 (e.g., the processor 220, the CPU 340, the processor 402, and/or one or more modules illustrated FIG. 5). The operations of the illustrated process presented below are intended to be illustrative. In some embodiments, the process 600 may be accomplished with one or more additional operations not described and/or without one or more of the operations herein discussed. Additionally, the order in which the operations of the process as illustrated in FIG. 6 and described below is not intended to be limiting.

In 610, the processing device 121 (e.g., the obtaining module 510) may obtain a plurality of sets of reference information relating to a diffusible substance from a plurality of devices (e.g., the plurality of devices 110) respectively.

As used herein, the diffusible substance refers to a substance that can diffuse directionally or non-directionally to cause a fire, an explosion, poisoning, etc. In some embodiments, the diffusible substance may include a gas (e.g., a flammable gas, a toxic gas), a liquid, a powder, or the like, or any combination thereof. The gas may include natural gas, hydrogen, carbonic oxide, sulfur dioxide, etc. The liquid may include oil, petroleum, gasoline, ethyl alcohol, etc. The powder may include flour, paper powder, wood powder, coal powder, metal powder, graphite powder, tea powder, fish powder, or the like, or any combination thereof.

In some embodiments, the plurality of sets of reference information may correspond to a same or a substantially same time domain.

In some embodiments, as described in connection with FIG. 1, each of the plurality of devices 110 may be connected to the processing device 121 via a network (e.g., a 5G network) which satisfies a predetermined time delay condition (e.g., a time delay of the network is less than a predetermined delay threshold such as 1 millisecond, 0.5 milliseconds). In this situation, the plurality of devices 110 may correspond to a same or a substantially same time domain. Accordingly, information (also referred to as "preliminary reference information") acquired by the plurality of devices 110 correspond to the same or substantially same time domain. The processing device 121 may obtain the plurality of sets of preliminary reference information directly from the plurality of devices 110 respectively via the network as the plurality of sets of reference information.

In some embodiments, a portion of the plurality of devices 110 may be connected to the processing device 121 via a network (e.g., a network with a time delay larger than the predetermined delay threshold) which does not satisfy the predetermined time delay condition. In this situation, the portion of the plurality of devices 110 may correspond to different time domains. Accordingly, the processing device 121 may obtain the plurality of sets of preliminary reference information relating to the diffusible substance from the plurality of devices 110 respectively. Then the processing device 121 may determine the plurality of sets of reference information relating to the diffusible substance by calibrating the plurality of sets of preliminary reference information to be corresponding to a same or a substantially same time domain. For example, each of the plurality of devices 110 may include a positioning sensor (which also can record time information) with a same type and same parameters. Accordingly, each of the plurality of sets of preliminary reference information may include at least a preliminary time point when a corresponding device 110 (e.g., the positioning sensor) detects the diffusible substance and a location when the corresponding device 110 (e.g., the positioning sensor) detects the diffusible substance. The processing device 121 may calibrate a plurality of preliminary time points to a same or substantially same time domain based on the type of the positioning sensor, the parameters of the positioning sensor, locations of the positioning sensors, and/or network parameter of the network.

In some embodiments, each of the plurality of sets of reference information may include a time point when a corresponding device detects the diffusible substance, a location where the corresponding device detects the diffusible substance.

In some embodiments, at least one of the plurality of sets of reference information may also include an indicator reflecting an amount of the diffusible substance at the time point when the diffusible substance is detected by the corresponding device and the location where the diffusible substance is detected by the corresponding device. For example, the diffusible substance may include a gas or a powder, accordingly, the indicator includes a concentration of the gas or the powder. As another example, the diffusible substance may include a liquid, accordingly, the indicator may include a hydraulic pressure of the liquid.

In some embodiments, at least one of the plurality of sets of reference information may also include sound information relating to the diffusible substance at the time point when the diffusible substance is detected by the corresponding device and the location where the diffusible substance is detected by the corresponding device.

In some embodiments, at least one of the plurality of sets of reference information may also include environmental information at the time point when the diffusible substance is detected by the corresponding device and the location where the diffusible substance is detected by the corresponding device. The environmental information may include a temperature, a humidity, a brightness, an air pressure, a wind direction, a wind speed, or the like, or any combination thereof.

In some embodiments, types of the plurality of sets of reference information may be the same, partially different, or totally different. For instance, each of the plurality of sets of reference information may include the time point when the diffusible substance is detected and the location where the diffusible substance is detected, some sets of the plurality of sets of reference information may also include the indicator reflecting the amount of the diffusible substance, and some other sets of the plurality of sets of reference information may also include environmental information.

For example, it is assumed that the plurality of devices 100 includes a first device and a second device. Accordingly, the plurality of sets of reference information includes a first set of reference information corresponding to the first device and a second set of reference information corresponding to the second device. Each of the first set of reference information and the second set of reference information includes a time point when the diffusible substance is detected by the first device or the second device and a location where the diffusible substance is detected by the first device or the second device. Besides, the first set of reference information also includes a temperature at a time point when the diffusible substance is detected by the first device and a location where the diffusible substance is detected by the first device; the second set of reference information also includes sound information (e.g., a sound relating to an explosion caused by the diffusible substance) at a time point when the diffusible substance is detected by the second device and a location where the diffusible substance is detected by the second device.

As another example, it is assumed that the plurality of devices 110 includes a first device, a second device, and a third device. Accordingly, the plurality of sets of reference information includes a first set of reference information corresponding to the first device, a second set of reference information corresponding to the second device, and a third set of reference information corresponding to the third device, each of which includes a time point when the diffusible substance is detected (e.g., by the first device, the second device, or the third device) and a location where the diffusible substance is detected (e.g., by the first device, the second device, or the third device). Besides, for the diffusible substance including a liquid, each of the first set of reference information, the second set of reference information, and the third set of reference information also includes a hydraulic pressure of the liquid at the time point when the diffusible substance is detected and the location where the diffusible substance is detected; for the diffusible substance including a gas or a powder, each of the first set of reference information, the second set of reference information, and the third set of reference information also includes a concentration of the gas at the time point when the diffusible substance is detected and the location where the diffusible substance is detected.

In 620, the processing device 121 (e.g., the diffusion trend determination module 520) may determine a diffusion trend of the diffusible substance based on the plurality of sets reference information.

In some embodiments, the diffusion trend may include a diffusion direction, a diffusion path, a diffusion speed, or the like, or any combination thereof. In some embodiments, the diffusion trend may also include an amount changing trend which refers to an amount vibration of the diffusible substance in time domain and/or space domain. In some embodiments, the processing device 121 may rank the plurality of sets of reference information based on a plurality of time points corresponding to the plurality of sets of reference information. Then the processing device 121 may determine the diffusion trend of the diffusible substance based on a ranking result.

For example, the processing device 121 may rank a plurality of locations corresponding to the plurality of sets of reference information according to a chronological order of the plurality of time points corresponding to the plurality of sets of reference information. Then processing device 121 may determine a diffusion path and/or a diffusion direction of the diffusible substance based on the ranked plurality of locations.

As another example, it is assumed that the diffusible substance includes a gas, the processing device 121 may rank a plurality of locations and a plurality of concentrations corresponding to the plurality of sets of reference information according to a chronological order of the plurality of time points corresponding to the plurality of sets of reference information. Then the processing device 121 may determine an amount changing trend (e.g., a concentration changing trend) of the gas in space domain based on the ranked plurality of concentrations and the ranked plurality of locations. Alternatively, the processing device 121 may determine an amount changing trend (e.g., a concentration changing trend) of the gas in time domain based on the ranked plurality of concentrations and the plurality of time points.

As a further example, it is assumed that the diffusible substance includes a liquid, the processing device 121 may determine an amount changing trend (e.g., a hydraulic pressure changing trend) of the liquid in space domain and/or time domain based on a plurality of time points, a plurality of locations, and a plurality of hydraulic pressures corresponding to the plurality of sets of reference information.

As a still further example, in some situations, the diffusion of the diffusible substance may cause an explosion. Each of the plurality of sets of reference information may include sound information relating to the explosion. For illustration purposes, it is assumed that the plurality of devices 110 include a device A, a device B, and a device C. Accordingly, other than time information and location information, the plurality of sets of reference information include first sound information relating to the explosion obtained from the device A, second sound information relating to the explosion obtained from the device B, and third sound information relating to the explosion obtained from the device C. The first sound information may correspond to a first time point when the device A detects a sound relating to the explosion and a first location where the device A detects the sound relating to the explosion. The second sound information may correspond to a second time point when the device B detects the sound relating to the explosion and a second location where the device B detects the sound relating to the explosion. The third sound information may correspond to a third time point when the device C detects a sound relating to the explosion and a third location where the device A detects the sound relating to the explosion. The processing device 121 may determine a location of the explosion based on the first time point, the second time point, the third time point, the first location, the second location, and the third location. Then the processing device 121 may determine the diffusion trend of the diffusible substance based on the location of the explosion.

As a still further example, as described in connection with above, the plurality of devices 110 may further include a device D. The plurality of sets of reference information may further include a temperature obtained from the device D. The temperature may correspond to a fourth time point when the device D detects the diffusible substance and a location where the device D detects the diffusible substance. The processing device 121 may determine the diffusible trend of the diffusible substance based on the temperature and the location of the explosion. More descriptions regarding the determination of the diffusion trend may be found elsewhere in the present disclosure (e.g., FIGS. 7 and 8 and the descriptions thereof).

In some embodiments, the processing device 630 (e.g., the response plane determination module) may determine a response plan for dealing with the diffusible substance based on the diffusion trend of the diffusible substance.

In some embodiments, the response plan may relate to a personnel evacuation, a prediction of potential danger, a dealing priority for different locations where the diffusible substance is detected, or the like, or any combination thereof. In some embodiments, the response plan may include a visualization of the diffusion trend. For example, the response plan may include information relating to the diffusion trend mapped on an electronic map and/or presented in a written form.

Take a leakage of a powder in a factory as an example, the powder may cause a fire and/or an explosion when meeting an open flame and/or high temperature. The processing device 121 may determine whether the diffusion direction of the powder is directed to a location (or region) where a working electronic device is located. In response to a determination that the diffusion direction of the powder is directed to the location (or region), the processing device 121 may determine the location (or region) as a priority area that needs priority attention. Alternatively, the processing device 121 may determine whether a temperature at a location (or region) where the powder with a relatively high concentration is detected is greater than a temperature threshold. In response to a determination that the temperature is greater than the temperature threshold, the processing device 121 may determine the location (or region) as a priority area. Further, the processing device 121 may generate an alert for alerting people surrounding the priority area to evacuate from the location (or region). Alternatively, the processing device 121 may transmit information relating to the priority area and/or the alert to a target terminal (e.g., the terminal device(s) 130) associated with a fireman and/or personnel in charge safety of the factory.

Take a leakage of a toxic gas as an example, the toxic gas may diffuse along multiple directions. The processing device 121 may determine a plurality of diffusion directions and/or amount changing trends of the toxic gas. The processing device 121 may determine whether one of the plurality of diffusion directions is directed to a location (or region) where one or more persons are located. In response to a determination that the diffusion direction is directed to the location (or region), the processing device 121 may determine the location (or region) as a priority area. In response to a determination that the diffusion direction is not directed to the location (or region), the processing device 121 may determine whether a concentration of the toxic gas corresponding to the diffusion direction is greater than a concentration threshold. In response to a determination that the concentration is greater than the concentration threshold, the processing device 121 may determine a location (or region) where the diffusion direction is directed to as a priority area. Further, the processing device 121 may generate an alert for alerting people surrounding the priority area to evacuate from the location (or region). Alternatively, the processing device 121 may transmit information relating to the priority area and/or the alert to a target terminal (e.g., the terminal device(s) 130) associated with a fireman and/or personnel in charge safety of the factory.

Take a leakage of petroleum in a tank as an example, the tank may include one or more pipes which cause the leakage of the petroleum. The petroleum may cause a fire when a temperature surrounding the petroleum is greater than a temperature threshold. It is assumed that a number count of the one or more pipes is 8, the petroleum may diffuse along at least 8 directions along the 8 pipes. The processing device 121 may determine whether a temperature at a location along one of the 8 directions is greater than the temperature threshold. In response to a determination that the temperature is greater than the temperature threshold, the processing device 121 may determine a pipe corresponding to the direction to be a priority pipe that needs priority attention. Further, the processing device 121 may transmit information regarding the priority pipe to a target terminal (e.g., the terminal device(s) 130) associated with a personnel in charge of a valve of the priority pipe.

According to some embodiments of the present disclosure, the processing device 121 may determine the diffusion trend and/or the response plan with multi-dimensional information relating to the diffusible substance taken into consideration, which can reflect a real situation of the diffusion of the diffusible substance comprehensively, thereby reducing the loss or hazard caused by the diffusion of the diffusible substance. For example, when a fire and/or an explosion happens in a region, the processing device 121 may obtain information relating to the fire and/or the explosion from multiple movable and/or fixedly mounted devices in and/or surrounding the region. The information relating to the fire and/or the explosion may correspond to a same or a substantially same time domain. Accordingly, according to the information corresponding to a same or a substantially same time domain, the processing device 121 can determine a location of the fire and/or the explosion, a diffusion trend of the fire and/or the explosion, a response plan for dealing with the fire and/or the explosion accurately and efficiently.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more additional operations may be added in the process 600 and/or one or more operations of the process 600 described above may be omitted. For example, the process 600 may include an additional operation for transmitting the response plan to one or more target terminals for further dealing with the diffusible substance.

Figure 7:
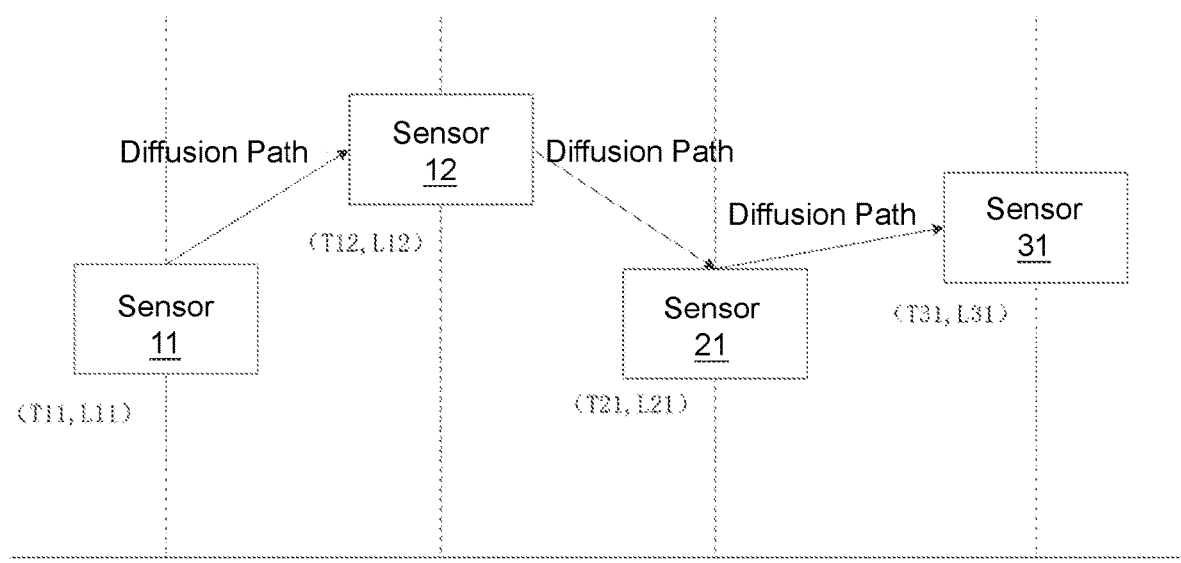
FIG. 7 is a schematic diagram illustrating an exemplary process for determining a diffusion trend of a harmful gas according to some embodiments of the present disclosure.

FIG. 7 is a schematic diagram illustrating an exemplary process for determining a diffusion trend of a harmful gas according to some embodiments of the present disclosure.

It is assumed that there are four devices each of which includes a sensor (e.g., a sensor 11, a sensor 12, a sensor 21, and a sensor 31) configured to detect the harmful gas. As described elsewhere in the present disclosure, the four devices are connected to the server 120 via a 5G network and correspond to a same or substantially same time domain.

As illustrated in FIG. 7, sensor 11 detects the harmful gas at a first time point T11 and a first location L11; the sensor 12 detects the harmful gas at a second time point T12 and a second location L12; the sensor 21 detects the harmful gas at a third time point T21 and a third location L21; the sensor 31 detects the harmful gas at a fourth time point T31 and a fourth location L31.

Accordingly, the processing device 121 may obtain four sets of reference information corresponding to the four devices respectively, which can be expressed as (T11, L11), (T12, L12), (T21, L21), and (T31, L31). The processing device 121 may rank the four sets of reference information according to a chronological order of corresponding time points. Then the processing device 121 may determine a diffusion direction, a diffusion path, and/or a diffusion speed of the harmful gas based on ranked reference information.

For example, as shown in FIG. 7, the diffusion direction or the diffusion path can be expressed as "L11–L12–L21–L31;" a global diffusion speed or an average diffusion speed can be expressed as a ratio of a global distance among the four locations (i.e., L11, L12, L21, and L31) to a time interval (T31–T11).

Figure 8:
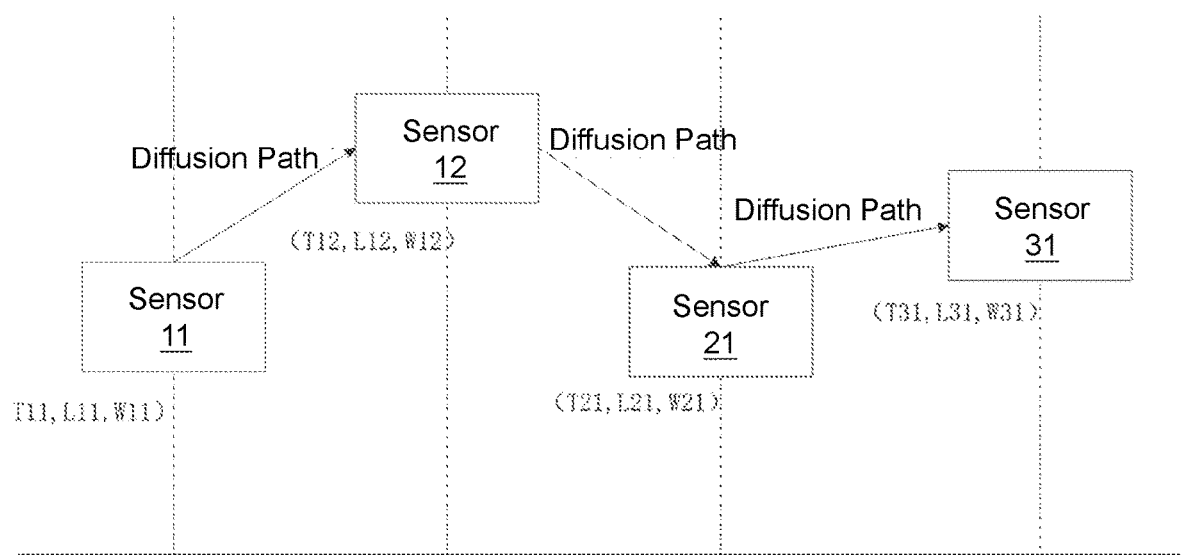
FIG. 8 is a schematic diagram illustrating an exemplary process for determining a diffusion trend of a harmful gas according to some embodiments of the present disclosure.

FIG. 8 is a schematic diagram illustrating an exemplary process for determining a diffusion trend of a harmful gas according to some embodiments of the present disclosure.

As described in connection with FIG. 7, each of the four devices may also include an amount sensor configured to determine an indicator indicating an amount of the diffusible substance. Accordingly, each of the four sets of reference information corresponding to the four devices also includes a concentration of the harmful gas at the time point when the harmful gas is detected and at a location where the harmful gas is detected, which can be expressed as (T11, L11, W11), (T12, L12, W12), (T21, L21, W21), and (T31, L31, W31). The processing device 121 may rank the four sets of reference information according to a chronological order of corresponding time points. Then, other than the diffusion direction, the diffusion path, and/or the diffusion speed, processing device 121 may also determine an amount changing trend of the harmful gas based on ranked reference information.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment," "one embodiment," or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer-readable media having computer-readable program code embodied thereon.

A computer-readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 1703, Perl, COBOL 1702, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a software as a service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for analyzing a diffusion trend of a diffusible substance, comprising:
   at least one storage device including a set of instructions; and
   at least one processor in communication with the at least one storage device, wherein when executing the set of instructions, the at least one processor is directed to cause the system to perform operations including:
      obtaining a plurality of sets of reference information relating to the diffusible substance from a plurality of devices respectively, each of the plurality of sets of reference information at least including a time point when a corresponding device detects the diffusible substance and a location where the device detects the diffusible substance, wherein the plurality of sets of reference information correspond to a same or a substantially same time domain; and
      determining the diffusion trend of the diffusible substance based on the plurality of sets reference information.

2. The system of claim 1, wherein the obtaining the plurality of sets of reference information relating to the diffusible substance from the plurality of devices respectively includes:
   obtaining, via a network satisfying a predetermined time delay condition, the plurality of sets of reference information relating to the diffusible substance from the plurality of devices respectively.

3. The system of claim 2, wherein a time delay of the network is less than a predetermined delay threshold.

4. The system of claim 1, wherein the obtaining the plurality of sets of reference information relating to the diffusible substance from the plurality of devices respectively includes:
   obtaining a plurality of sets of preliminary reference information relating to the diffusible substance from a plurality of devices respectively; and
   determining the plurality of sets of reference information relating to the diffusible substance by calibrating the plurality of sets of preliminary reference information to be corresponding to a same or a substantially same time domain.

5. The system of claim 1, wherein each of the plurality of sets of reference information further includes an indicator reflecting an amount of the diffusible substance at the time point when the diffusible substance is detected by the corresponding device and the location where the diffusible substance is detected by the corresponding device.

6. The system of claim 5, wherein:
   the diffusible substance includes a gas or a powder, and the indicator includes a concentration of the gas or the powder; or
   the diffusible substance includes a liquid, and the indicator includes a hydraulic pressure of the liquid.

7. The system of claim 1, wherein each of the plurality of sets of reference information further includes sound information relating to the diffusible substance at the time point when the diffusible substance is detected by the corresponding device and the location where the diffusible substance is detected by the corresponding device.

8. The system of claim 1, wherein each of the plurality of sets of reference information further includes environmental information at the time point when the diffusible substance is detected by the corresponding device and the location where the diffusible substance is detected by the corresponding device.

9. The system of claim 8, wherein the environmental information includes at least one of a temperature, a humidity, a brightness, an air pressure, a wind direction, or a wind speed.

10. The system of claim 1, wherein the diffusion trend includes at least one of a diffusion direction, a diffusion speed, or a diffusion path.

11. The system of claim 1, wherein the determining the diffusion trend of the diffusible substance based on the plurality of sets reference information includes:
   ranking the plurality of sets of reference information based on a plurality of time points corresponding to the plurality of sets of reference information; and
   determining the diffusion trend of the diffusible substance based on a ranking result.

12. The system of claim 1, wherein the operations further comprise:
   determining, based on the diffusion trend of the diffusible substance, a response plan for dealing with the diffusible substance.

13. The system of claim 12, wherein the operations further comprise:
   transmitting the response plan to a target terminal.

14. A method for analyzing a diffusion trend of a diffusible substance, the method being implemented on a computing device including at least one processor and at least one storage device, the method comprising:
   obtaining a plurality of sets of reference information relating to the diffusible substance from a plurality of devices respectively, each of the plurality of sets of reference information at least including a time point when a corresponding device detects the diffusible substance and a location where the device detects the diffusible substance, wherein the plurality of sets of reference information correspond to a same or a substantially same time domain; and determining the diffusion trend of the diffusible substance based on the plurality of sets reference information.

15. A system for analyzing a diffusion trend of a diffusible substance, comprising:
a plurality of devices each of which is configured to detect a set of reference information relating to the diffusible substance, the set of reference information at least including a time point when a corresponding device detects the diffusible substance and a location where the device detects the diffusible substance, wherein the plurality of devices correspond to a same or a substantially same time domain; and
at least one processor configured to
obtain, via a network, the plurality of sets of reference information from the plurality of devices respectively; and
determine the diffusion trend of the diffusible substance based on the plurality of sets of reference information.

16. The system of claim 15, wherein a time delay of the network is less than a predetermined delay threshold.

17. The system of claim 15, wherein each of the plurality of devices includes a positioning sensor configured to detect the location where the corresponding device detects the diffusible substance and a substance sensor configured to detect whether the diffusible substance exists.

18. The system of claim 15, wherein each of the plurality of devices includes an amount sensor configured to determine an indicator indicating an amount of the diffusible substance at the time point when the diffusible substance is detected by the corresponding device and the location where the diffusible substance is detected by the corresponding device.

19. The system of claim 15, wherein each of the plurality of devices includes a sound sensor configured to determine sound information relating to the diffusible substance at the time point when the diffusible substance is detected by the corresponding device and the location where the diffusible substance is detected by the corresponding device.

20. The system of claim 15, wherein each of the plurality of devices includes at least one of a temperature sensor, a humidity sensor, a brightness sensor, an air pressure sensor, or a wind sensor, which is configured to determine environmental information relating to the diffusible substance at the time point when the diffusible substance is detected by the corresponding device and the location where the diffusible substance is detected by the corresponding device.

* * * * *